United States Patent [19]

Broadhurst et al.

[11] 4,431,594
[45] Feb. 14, 1984

[54] METHOD FOR PREPARATION OF SALTS OF N-PHOSPHONOMETHYLGLYCINE

[75] Inventors: Michael D. Broadhurst, Fairfield, Conn.; James B. Heather, Hercules, Calif.

[73] Assignee: Stauffer Chemical Company, Westport, Conn.

[21] Appl. No.: 457,812

[22] Filed: Jan. 13, 1983

[51] Int. Cl.³ .............................................. C07F 9/38
[52] U.S. Cl. .................. 260/502.5 F; 260/501.12
[58] Field of Search ............... 260/502.5 F, 501.12, 260/501.15

[56] References Cited

U.S. PATENT DOCUMENTS

| | | | |
|---|---|---|---|
| 2,271,707 | 2/1942 | Munz et al. | 260/501.15 |
| 2,831,019 | 4/1958 | Erskine | 260/501.15 |
| 4,147,719 | 4/1979 | Franz | 260/502.5 F |
| 4,196,143 | 4/1980 | Strycker | 260/501.12 |
| 4,315,765 | 2/1982 | Large | 260/502.5 F |
| 4,341,549 | 7/1982 | Large et al. | 260/502.5 F |

*Primary Examiner*—J. E. Evans
*Attorney, Agent, or Firm*—Paul R. Martin

[57] ABSTRACT

A process for the preparation of sulfonium or sulfoxonium salts of N-phosphonomethylglycine which comprises:

(1) reacting N-phosphonomethylglycine, a compound of the formula

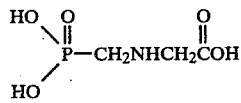

with a compound selected from the group consisting of those having the formula

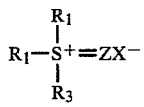 (a)

wherein $R_1$, $R_2$ and $R_3$ are the same or different and are alkyl groups having from 1 to 4 carbon atoms or aromatic alkyl groups, X is chloride, bromide or iodide and Z is an electron pair or oxygen, or

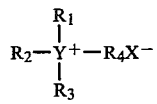 (b)

wherein $R_1$, $R_2$ and $R_3$ are the same or different and are alkyl groups having from 1 to 4 carbon atoms and are the same as in (a) above, $R_4$ is an alkyl group having from 1 to 12 carbon atoms, aromatic or aromatic alkyl groups, X is chlorine or iodine, and Y is nitrogen or phosphorus, said reaction being conducted in the presence of a trialkylamine of the formula

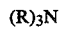 $(R)_3N$ wherein each R is the same or different and is an alkyl group ranging from 4 to 13 carbon atoms, all in the presence of water and a polar functional organic solvent which is immiscible in water, said reaction being conducted at a temperature and for a sufficient period of time to cause completion of the reaction, and (2) isolating the end product by phase separation.

9 Claims, No Drawings

METHOD FOR PREPARATION OF SALTS OF N-PHOSPHONOMETHYLGLYCINE

BACKGROUND OF THE INVENTION

This invention relates to a novel method for the preparation of trialkylsulfonium, sulfoxonium, and nitrogen or phosphorus based organic quaternary salts of N-phosphonomethylglycine, compounds which are known herbicides and plant growth regulators.

Herbicides are widely used by farmers, commercial agricultural companies, and other industries in order to increase crop yields for such staple crops as corn, soybeans, rice, and the like, and to eliminate weed growth along highways, railroad rights-of-way, and other areas. Herbicides are effective in killing or controlling unwanted weeds which compete for soil nutrients with the crop plants, and by reason of the fact that they kill weeds, are responsible for improving the aesthetic appearance of highway and railroad rights-of-way. There are a number of different types of herbicides presently sold commercially, and these fall into two general categories. The categories are pre-emergence and post-emergence herbicides. The pre-emergence herbicides are applied to the soil prior to the emergence of the weed plants from the soil, and the post-emergence herbicides are applied to plant surfaces after emergence of the weeds or other unwanted plants from the soil.

One of the earliest post-emergence herbicides used commercially was 2,4-D (2,4-dichlorophenoxyacetic acid). After a number of years of use of this and similar compounds such as 2,4,5-T (2,4,5-trichlorophenoxy acetic acid), it was found that certain decomposition products of these herbicides were long lasting and were not biodegradable. While there has been some dispute between governmental agencies and commercial interests regarding the effects of residual products of 2,4-D, 2,4,5-T and similar compounds, the agencies nevertheless restricted the use of these herbicides in the United States some years ago. Since that time, efforts have been made to develop herbicides which are biodegradable into harmless residues within a relatively short time after their application.

One such compound, which has been found to be biodegradable, yet which is effective as a herbicide and plant growth regulator when employed at lower rates, is N-phosphonomethylglycine and various salts thereof. The N-phosphonomethylglycine and agriculturally effective salts have been approved for use by the U.S. Government, and, as a consequence, this herbicide has become extremely successful commercially.

The N-phosphonomethylglycine and certain salts are the only effective and approved post-emergence herbicides in the field. The present commercial compound is the isopropylamine salt of N-phosphonomethylglycine and derivatives thereof. In field use it is normally applied in amounts of from 0.01 to about 20 pounds per acre, preferably from 2 to 6 pounds per acre.

The N-phosphonomethylglycines, and certain soluble salts thereof, can be made in a number of different ways. One such method, as described in U.S. Pat. No. 3,160,632 (Toy et al., Dec. 8, 1964) is to react N-phosphinomethylglycine (glycinemethylenephosphinic acid) with mercuric chloride in a water solvent at reflux temperature, and subsequently separating the reaction products. Another method is the reaction of ethyl glycinate with formaldehyde and diethylphosphite. The latter method is described in U.S. Pat. No. 3,799,758 (Franz, Mar. 26, 1974). In addition, there is a whole series of patents, relating to N-phosphonomethylglycines, their salts, and derivatives thereof, described as being useful herbicides and plant growth regulators. Such additional patents relating to the N-phosphonomethylglycines, methods of application, methods of preparation, salts, and derivatives, include U.S. Pat. No. 3,868,407, U.S. Pat. No. 4,197,254, and U.S. Pat. No. 4,199,354, among others.

The trialkylsulfonium and sulfoxonium salts of N-phosphonomethylglycine have also been found to be useful as plant growth regulators and herbicides. These salts are described in U.S. Pat. No. 4,315,765, Large. As disclosed in that patent, the compounds can be prepared from N-phosphonomethylglycine by reacting the latter with silver oxide to form the silver salts or with sodium hydroxide to form the sodium salt, and treating either the silver or sodium salt with a trialkylsulfonium or sulfoxonium halide. It is desirable to simplify this process to make it unnecessary to isolate intermediate products, and the process of the presant invention is directed to that end in order to simplify and make less expensive the process for the production of the sulfonium and sulfoxonium salts, and for certain nitrogen or phosphorus based organic quaternary salts.

SUMMARY OF THE INVENTION

It has now been discovered that the sulfonium and sulfoxonium salts and other nitrogen or phosphorus based organic quaternary salts of N-phosphonomethylglycine can be produced by:

(1) reacting N-phosphonomethylglycine, a compound of the formula

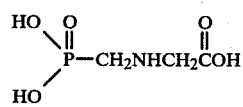

with a compound selected from the group consisting of those having the formula

wherein $R_1$, $R_2$ and $R_3$ are the same or different and are alkyl groups having from 1 to 4 carbon atoms or aromatic alkyl groups, X is chloride, bromide or iodide and Z is an electron pair or oxygen, or

wherein $R_1$, $R_2$ and $R_3$ are the same or different and are alkyl groups having from 1 to 4 carbon atoms and are the same as in (a) above, $R_4$ is an alkyl group having from 1 to 12 carbon atoms, aromatic or aromatic alkyl groups, X is chloride, bromide or iodide, and Y is nitrogen or phosphorus, said reaction being conducted in the presence of a trialkylamine of the formula

wherein each R is the same or different and is an alkyl group ranging from 4 to 13 carbon atoms, all in the presence of water and a polar water-immiscible organic solvent, and (2) isolating the end product by phase separation.

Preferred compounds of formula (a) set forth above for use in the process of the invention include trimethylsulfonium chloride, trimethylsulfoxonium chloride, and trimethylsulfonium iodide, with the most preferred compound being trimethylsulfonium chloride.

Preferred compounds having formula (b) as set forth above, include tetramethylammonium chloride, benzyltributylammonium chloride, tetrabutylammonium iodide, and benzyl triphenylphosphonium chloride, with the most preferred compound being tetramethylammonium chloride.

Preferred trialkylamines for use in the process of the invention include those with alkyl groups (straight chain or branched) having 8 to 10 carbon atoms. Commercial blends which are predominantly $C_8$ to $C_{10}$ such as Alamine ® 336, manufactured by the Henkel Co., Minneapolis, Minn., are economically advantageous and most preferred.

Other suitable amines include tributylamine, tripentylamine, trihexylamine, triheptylamine and triisodecylamine.

There are certain factors to be observed which are critical to the success of the process of the invention.

The starting compound is N-phosphonomethylglycine. This compound can be purchased commercially or it can be made in any number of different ways as referred to previously herein.

The trialkyl amine which is also used as a component in the process of the invention, must be one which itself is substantially water-insoluble and forms a water-insoluble salt with the HCl (hydrogen chloride) which is removed from the N-phosphonomethylglycine and the organic sulfur, nitrogen or phosphorus salt in order to produce the sulfonium or sulfoxonium salts or quaternary ammonium or phosphonium salts which are the end products of the process of the invention.

The solvent for the reactants of the process as indicated must be one which is water-immiscible. A suitable solvent has been found to be a combination of toluene and amyl alcohol in the 7:3 ratio by weight, however, the exact ratio of these two solvents is not critical. Other suitable solvents include methylene chloride, 1,2-dichloroethane, methylisobutyl ketone, isobutyl alcohol, and n-amyl alcohol. The solvent must be one which is polar and is substantially water-immiscible. A nonpolar co-solvent may be used to improve the selectivity of the process with regard to limiting the production of undesired by-products.

Using the preferred reactants, the process of the invention can be represented in accordance with the following formula.

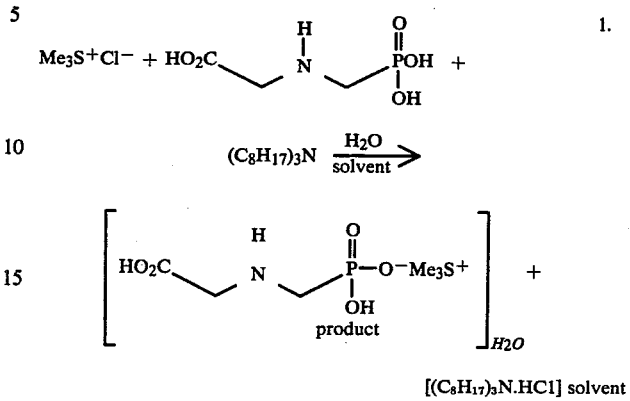

In carrying out the process of the invention, the N-phosphonomethylglycine and trimethylsulfonium chloride are reacted in approximately stoichiometric amounts, while the amine is present in excess.

The amount of solvent used must be sufficient to facilitate phase separation of the components, and generally speaking an excess of the solvent is desirable.

Preferably, the reaction is conducted at temperatures ranging from about 20° to about 40° C., and for a period of time ranging from about ½ to about 4 hours.

This invention will be more clearly understood with reference to the following example which serves to illustrate the invention but is not intended to limit it thereby.

EXAMPLE I

A round-bottom flask was obtained, and to that flask was added 8.62 grams (g) of 98.1% phosphonomethylglycine (0.05 mole) slurried in 12 milliliters (ml) of water, and to this was added 7.7 g of a 72.9% aqueous solution of trimethylsulfonium chloride (5.63 g, 0.05 mole) and 29.4 g of Alamine ® 336 (1.5 equivalents) in 55 ml of toluene and 25 ml of amyl alcohol. This mixture was stirred vigorously and with continued stirring, all of the phosphonomethylglycine dissolved.

The mixture was then phase separated, and the aqueous (lower) phase (23.7 g) was then concentrated under reduced pressure, yielding 18.75 g of product which was an aqueous solution found to be 65% by weight of the sulfonium salt of phosphonomethylglycine.

Additional runs were done, in which the solvent and the chloride compound was varied in accordance with Table I below. In Table I, the starting compound, solvents, and various other constituents are set forth with the reaction conditions and the yield of product indicated.

TABLE I

Summary of Runs

| Amine | Amount of Amine | | Salt used with PMG* | Solvent % mixture by weight | Yield |
|---|---|---|---|---|---|
| | 1st Wash (equiv.) | 2nd Wash (equiv.) | | | |
| Alamine 336 | 1.5 | — | trimethylsulfonium iodide | 70% toluene 30% n-amyl alcohol | 72% |
| Alamine 336 | 1.5 | — | benzyltributyl-ammonium chloride | 90% toluene 30% n-amyl alcohol | 67% |
| Alamine 336 | 1.5 | — | tetramethylammonium | 70% toluene | 64% |

TABLE I-continued

Summary of Runs

| Amine | Amount of Amine 1st Wash (equiv.) | Amount of Amine 2nd Wash (equiv.) | Salt used with PMG* | Solvent % mixture by weight | Yield |
|---|---|---|---|---|---|
| | | | chloride | 30% n-amyl alcohol | |
| Alamine 336 | 1.5 | — | tetrabutylammonium iodide | 70% toluene 30% n-amyl alcohol | 40% |
| Alamine 336 | 1.5 | — | benzyltriphenyl-phosphonium chloride | 70% toluene 30% n-amyl alcohol | 74% |
| Alamine 336 | 1.3 | 1.3 | trimethylsulfonium chloride | 1,2-dichloro-ethane | 84% |
| di(2-ethyl-hexyl)amine | 1.25 | 0.25 | trimethylsulfonium chloride | 1,2-dichloro-ethane | 80% |
| trioctylamine | 1.5 | 1.0 | trimethylsulfonium chloride | amyl alcohol | 71% |
| trioctylamine | 1.5 | 1.0 | trimethylsulfonium chloride | isobutyl alcohol | 69% |
| trioctylamine | 2.25 | 1.0 | trimethylsulfonium chloride | methyliso-butyl ketone | 86% |
| trioctylamine | 1.5 | 1.0 | trimethylsulfonium chloride | 2-ethyl-1-ketone | 82% |
| trioctylamine | 1.5 | 1.0 | trimethylsulfonium chloride | dichloro-methane | 89% |
| di(2-ethyl-hexyl)amine | 1.5 | 1.0 | trimethylsulfonium chloride | 2-ethyl-1-hexanol | 66% |
| Alamine 336 | 1.5 | 1.0 | trimethylsulfonium chloride | methyl iso-butyl ketone | 76% |
| Adogen 382 ® tri(iso-decyl)amine | 1.5 | 1.0 | trimethylsulfonium chloride | 1,2-dichloro-ethane | 60% |
| Alamine 308 ® tri(iso-octyl)amine | 1.5 | 1.0 | trimethylsulfonium chloride | 1,2-dichloro-ethane | 89% |
| trioctylamine | 1.5 | 1.0 | trimethylsulfonium chloride | 70% toluene 30% n-amyl alcohol | 88% |
| trioctylamine | 1.5 | 1.0 | trimethylsulfonium chloride | 50% toluene 50% n-amyl alcohol | 89% |
| Alamine 308 ® tri(iso-octyl)amine | 1.5 | 1.0 | trimethylsulfonium chloride | 70% toluene 30% n-amyl alcohol | 91% |
| Alamine 336 | 1.5 | — | trimethylsulfonium chloride | 70% toluene 30% n-amyl alcohol | 91% |

*PMG - phosphonomethylglycine

In the process of the invention, as set forth above, the N-phosphonomethylglycine and trimethylsulfonium chloride are first mixed in water with the amine, all in the presence of a water-immiscible solvent. The amine hydrochloride, formed in accordance with formula 1 is extracted into the organic phase by virtue of its low aqueous solubility, leaving the end product, the trialkyl-sulfonium or sulfoxonium salts of N-phosphonomethylglycine or other organic salts in the aqueous phase without contamination by foreign ions. The method as described above is advantageous over others, which require the formation of intermediate compounds which in themselves must be separated in order to carry out various steps of the process.

It will be recognized by those skilled in the art that variations in the quantities of reactants, temperatures used, mole ratios used, and time of reaction can be made in the method of the invention without departing from the spirit and scope of the appended claims.

What is claimed is:

1. A process for the preparation of organic salts of N-phosphonomethylglycine which comprises:
   (1) reacting N-phosphonomethylglycine, a compound of the formula

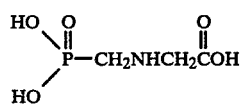

with a compound selected from the group consisting of those having the formula

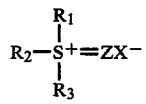
(a)

wherein $R_1$, $R_2$ and $R_3$ are the same or different and are alkyl groups having from 1 to 4 carbon atoms or aromatic alkyl groups, X is chloride, bromide or iodide and Z is an electron pair or oxygen, or

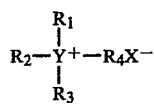
(b)

wherein $R_1$, $R_2$ and $R_3$ are the same or different and are alkyl groups having from 1 to 4 carbon atoms and are the same as in (a) above, $R_4$ is an alkyl group having from 1 to 12 carbon atoms, aromatic or aromatic alkyl groups, X is chloride, bromide or iodide, and Y is nitrogen or phosphorus, said reaction being conducted in the presence of a trialkylamine of the formula $$(R)_3N$$

wherein each R is the same or different and is an alkyl group ranging from 4 to 13 carbon atoms, all in the presence of water and a polar functional organic solvent which is immiscible in water, said reaction being conducted at a temperature and for a sufficient period of time to cause completion of the reaction, and (2) isolating the end product by phase separation.

2. The process according to claim 1 in which the amine is comprised of those having $C_8$ to $C_{10}$ alkyl groups.

3. The process of claim 1 in which the organic solvent is a mixture of toluene and amyl alcohol.

4. The process of claim 1 in which the N-phosphonomethylglycine and compounds of (a) or (b) are present in substantially stoichiometric amounts.

5. The process of claim 1 in which the alkyl amine is present in excess.

6. The process of claim 1 in which the temperature of the reaction is maintained between about 10° and about 40° C.

7. The process of claim 1 in which the time of the reaction ranges from about ½ to about 4 hours.

8. The process of claim 1 in which (a) is trimethylsulfonium chloride.

9. The process of claim 1 in which (a) is trimethylsulfoxonium chloride.

* * * * *